US010842988B2

(12) United States Patent
Thompson-Nauman et al.

(10) Patent No.: US 10,842,988 B2
(45) Date of Patent: Nov. 24, 2020

(54) OVER-THE-WIRE DELIVERY OF A SUBSTERNAL LEAD

(71) Applicant: Medtronic, Inc., Minneapolis, MN (US)

(72) Inventors: Amy E. Thompson-Nauman, Ham Lake, MN (US); James K. Carney, Roseville, MN (US); Melissa G. T. Christie, Andover, MN (US); Kenneth C. Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 108 days.

(21) Appl. No.: 14/293,309

(22) Filed: Jun. 2, 2014

(65) Prior Publication Data
US 2015/0342627 A1 Dec. 3, 2015

(51) Int. Cl.
*A61N 1/05* (2006.01)
*A61B 17/32* (2006.01)
*A61B 17/34* (2006.01)

(52) U.S. Cl.
CPC .............. *A61N 1/05* (2013.01); *A61N 1/0504* (2013.01); *A61B 17/3415* (2013.01); *A61B 2017/320056* (2013.01)

(58) Field of Classification Search
CPC .................... A61N 1/05; A61N 1/0504; A61N 1/056–0597; A61B 2017/320056; A61B 17/3468
See application file for complete search history.

(56) References Cited

U.S. PATENT DOCUMENTS

| 4,030,509 | A | | 6/1977 | Heilman et al. |
| 4,270,549 | A | | 6/1981 | Heilman |
| 4,291,707 | A | | 9/1981 | Heilman et al. |
| 4,765,341 | A | | 8/1988 | Mower et al. |
| 4,991,578 | A | * | 2/1991 | Cohen .................. A61N 1/0587 607/2 |

(Continued)

FOREIGN PATENT DOCUMENTS

| WO | 9315791 A1 | 8/1993 |
| WO | 2001023035 A1 | 4/2001 |

(Continued)

OTHER PUBLICATIONS

Ganapathy et al., "Implantable Device to Monitor Cardiac Activity with Sternal Wires," Pace, vol. 37, Dec. 2014, 11 pages.

(Continued)

*Primary Examiner* — Shaun L David
(74) *Attorney, Agent, or Firm* — Christopher & Weisberg, P.A.

(57) ABSTRACT

A method for implanting a medical lead. The method includes advancing a tunneling tool posteriorly proximate the caudal end of the sternum toward a first location. The tunneling tool is advanced superiorly underneath the sternum through the anterior mediastinum from the first location to a second location cranial to the first location. A guidewire is advanced from the first location to the second location. A medical lead is slid along at least a portion of the guidewire, the medical lead at least substantially spanning the distance between the first location and the second location.

17 Claims, 12 Drawing Sheets

(56) References Cited

U.S. PATENT DOCUMENTS

| | | | |
|---|---|---|---|
| 5,176,135 | A | 1/1993 | Fain et al. |
| 5,336,252 | A | 8/1994 | Cohen |
| 5,509,924 | A | 4/1996 | Paspa et al. |
| 5,634,895 | A * | 6/1997 | Igo .................. A61M 25/10 604/20 |
| 5,690,648 | A | 11/1997 | Fogarty et al. |
| 5,803,928 | A | 9/1998 | Tockman et al. |
| 5,827,216 | A * | 10/1998 | Igo .................. A61B 17/00234 604/176 |
| 5,902,331 | A | 5/1999 | Bonner et al. |
| 6,018,684 | A * | 1/2000 | Bartig .................. A61N 1/056 600/374 |
| 6,032,079 | A | 2/2000 | KenKnight et al. |
| 6,059,750 | A * | 5/2000 | Fogarty .................. A61M 1/1068 601/153 |
| 6,512,958 | B1 | 1/2003 | Swoyer et al. |
| 6,647,291 | B1 * | 11/2003 | Bonner .................. A61N 1/0563 607/123 |
| 6,749,574 | B2 | 6/2004 | O'Keefe |
| 7,288,096 | B2 | 10/2007 | Chin |
| 7,319,905 | B1 * | 1/2008 | Morgan .................. A61N 1/0587 607/129 |
| 7,398,781 | B1 * | 7/2008 | Chin .................. A61B 17/00008 128/898 |
| 7,655,014 | B2 | 2/2010 | Ko et al. |
| 7,846,088 | B2 | 12/2010 | Ness |
| 8,157,813 | B2 | 4/2012 | Ko et al. |
| 8,460,181 | B2 * | 6/2013 | Saadat .................. A61B 1/00085 396/17 |
| 2002/0147487 | A1 * | 10/2002 | Sundquist .................. A61N 1/056 607/122 |
| 2003/0014016 | A1 | 1/2003 | Purdy |
| 2003/0088212 | A1 * | 5/2003 | Tal .................. A61B 17/3415 604/163 |
| 2003/0093104 | A1 | 5/2003 | Bonner et al. |
| 2004/0143284 | A1 | 7/2004 | Chin |
| 2006/0116746 | A1 | 6/2006 | Chin |
| 2007/0239244 | A1 | 10/2007 | Morgan |
| 2008/0046056 | A1 | 2/2008 | O'Connor |
| 2008/0132979 | A1 | 6/2008 | Gerber |
| 2009/0264780 | A1 | 10/2009 | Schilling |
| 2010/0056858 | A1 | 3/2010 | Mokelke et al. |
| 2012/0029335 | A1 | 2/2012 | Sudam et al. |
| 2012/0191106 | A1 | 7/2012 | Ko et al. |
| 2013/0073022 | A1 | 3/2013 | Ollivier |

FOREIGN PATENT DOCUMENTS

| | | | |
|---|---|---|---|
| WO | 2004073506 | A2 | 9/2004 |
| WO | 2005032650 | A1 | 4/2005 |
| WO | 2006116595 | A1 | 11/2006 |
| WO | 2014036317 | A2 | 3/2014 |

OTHER PUBLICATIONS

Guenther et al., "Substernal Lead Implantation: A Novel Option to Manage DFT Failure in S-ICD patients," Clinical Research Cardiology, Published On-line Oct. 2, 2014, 3 pages.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

Edwin E. Vyhmeister, MD., et al, Simple Approach for Extrapericardial Placement of Defibrillator Patches via Median Sternotomy, The Annals of Thoracic Surgery, ats.ctsnetjournals.org, May 6, 2013.

Ralph J. Damiano, Jr., M.D., et al., Implantation of Cardioverter Defibrillators in the Post-Sternotomy Patient, The Annals of Thoracic Surgery, ats.ctsnetjournals.org, May 6, 2013, pp. 978-983.

Stephen W. Ely, Ph.D., M.D., et al., Thoracoscopic Implantation of the Implantable Cardioverter Defibrillator, Minimally Invasive Techniques, Chest / 103, chestioumal.chestpubs.org, May 6, 2013, p. 271-272.

Gerald M. Lawrie, M.D., et al., Right Mini-thoracotomy: An Adjunct to Left Subcostal Automatic Implantable Cardioverter Defibrillator Implantation, The Annals of Thoracic Surgery, ats. ctsnetjournals.org, May 6, 2013, pp. 780-781.

Donald Nuss, MB, ChB, FRCS(c), FACS, FAAP, Recent Experiences with Minimally Invasive Pectus Excavatum Repair "Nuss Procedure", The Japanese Journal of Thoracic and Cardiovascular Surgery, pp. 338-344.

Sony Jacob, M.D., et al., Percutaneous Epicardial Defibrillation Coil Implantation, A Viable Technique to Manage Refractory Defibrillation Threshold, Images and Case Reports in Arrhythmia and Electrophysiology, Circulation Arrhythmia and Electrophysiology published by The American Heart Association, Jan. 7, 2014, pp. 214-217.

Robert L. Quigley, M.D., et al., Migration of an Automatic Implantable Cardioverter-Defibrillator Patch Causing Massive Hemothorax, Texas Heart Institute Journal, Hemothorax Caused by Automatic ICD Patch Migration, vol. 23, No. 1, 1996.

E. Cigna, et al., A new technique for substernal colon transposition with a breast dissector: Report of 39 cases, Journal of Plastic, Reconstructive & Aesthetic Surgery (2006) 59, pp. 343-346.

Steven R. Mickelsen, et al., Transvenous Access to the Pericardial Space: A Novel Approach to Epicardial Lead Implantation for Cardiac Resynchronization Therapy, National Institute of Health Pacing Clin Electrophysiol, Oct. 2005; 28(10): 1018-1024.

JF Obadia, et al., New approach for implantation of automatic defibrillators using videothoracoscopy: Ann Cardiol Angeiol (Paris). Sep. 1994; 43(7):384-8.

John H. Lemmer, Jr., MD, Defibrillator Patch Constriction, Ann Thorac Surg 1996;61:1038-44.

Sandeep Nathan, MD, et al., Erosion of an Extrapericardial Implantable Cardioverter Defibrillator Patch Through the Gastric Fundus With Fistulous Tract Formation, Cardiology in Review 2006;14: e21-e23.

Deirdre Harman, et al., Differences in the Pathological Changes in Dogs' Hearts After Defibrillation with Extrapericardial Paddles and Implanted Defibrillator Electrodes, PACE vol. 14, February, Part II 1991: 358-61.

Jean-Francois Obadia, et al., Thoracoscopic Approach to Implantable Cardioverter Defibrillator Patch Electrode Implantation, Pace, vol. 19, Jun. 1996, 955-959.

Oz M. Shapira, et al., A Simplified Method for Implantation of Automatic Cardioverter Defibrillator in Patients with Previous Cardiac Surgery, PACE, vol. 16, January, Part 1 1993, 3-7.

Shreekanth V. Karwande, MD, et al., Bilateral Anterior Thoracotomy for Automatic Implantable Cardioverter Defibrillator Placement in Patients With Previous Sternotomy, Ann Thorac Surg 1992;54:791-3.

Rosemary Frame, et al., Long-Term Stability of Defibrillation Thresholds with Intrapericardial Defibrillator Patches, PACE, vol. 16, January, Part II 1993, 208-12.

JD Mitchell, et al., Experience with an implantable tiered therapy device incorporating antitachycardia pacing and cardioverter/ defribrillator therapy. The Journal of Thoracic and Cardiovascular Surgery, Mar. 1993; vol. 105(3), pp. 453-62; discussion 462-3.

SF Bolling, et al., Automatic internal cardioverter defibrillator: a bridge to heart transplantation. The Journal of Heart and Lung Transplantation: The Official Publication of the International Society for Heart Transplantation, Jul.-Aug. 1991; vol. 10(4), pp. 562-566.

William E. Steinke, M.D., et al., Subepicardial Infarction, Myocardial Impression, and Ventricular Penetration by Sutureless Electrode and Leads, CHEST, 70: Jul. 1, 1976: 80-1.

Stanford Hospital & Clinics, Epcardial Ablation, http://stanfordhospital.org/cardiovascularhealth/arrhythmia/treatments/ablation/epicardial-ablation.html.

Medtronic, Attain Biopolar OTW 4194, Technical Manual, A04287001, Feb. 5, 2004.

Medtronic, 6996T Tunneling Tool, Technical Manual, UCX19842001 198462001, Sep. 2001.

Medtronic, Attain Command + Surevalve 6250VC, 6250VS, Technical Manual, M7314176001 1A, Aug. 27, 2012.

(56) References Cited

OTHER PUBLICATIONS

Bielefeld, MR et al, Thoracoscopic placement of implantable cardioverter-defibrillator patch leads in sheep. http://www.ncbi.nlm.nih.gov/pubmed/8222192.
(PCT/US2015/033116) PCT Notification of Transmittal of the International Search Report and the Written Opinion of the International Searching Authority, dated Sep. 15, 2015, 8 pages.

* cited by examiner

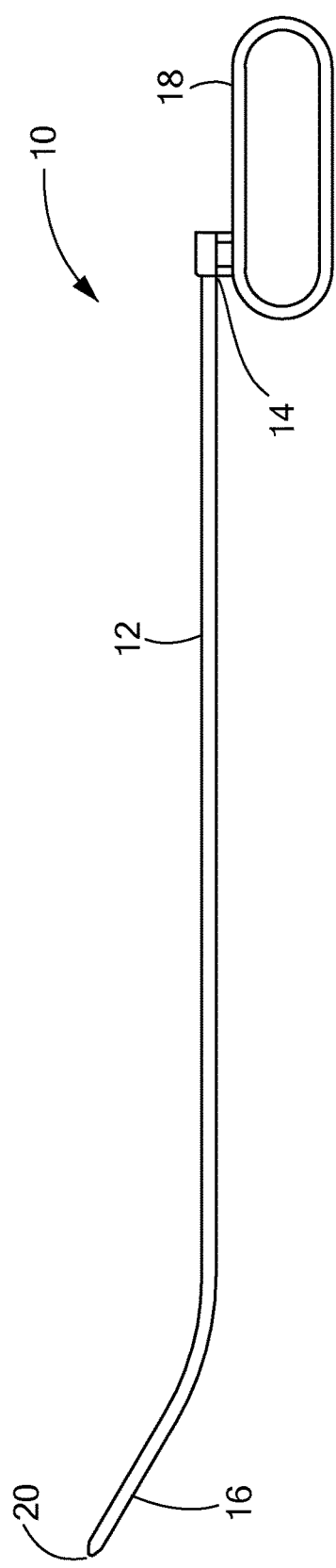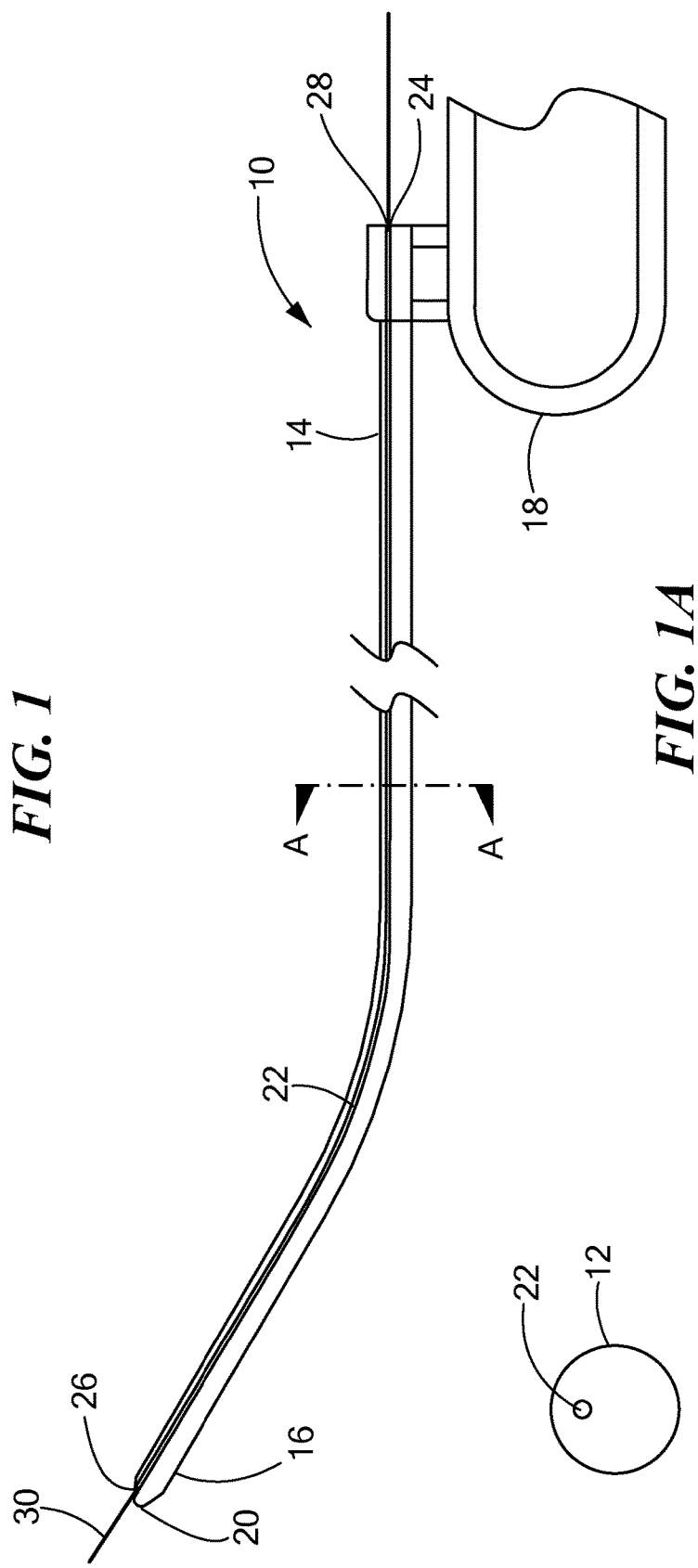

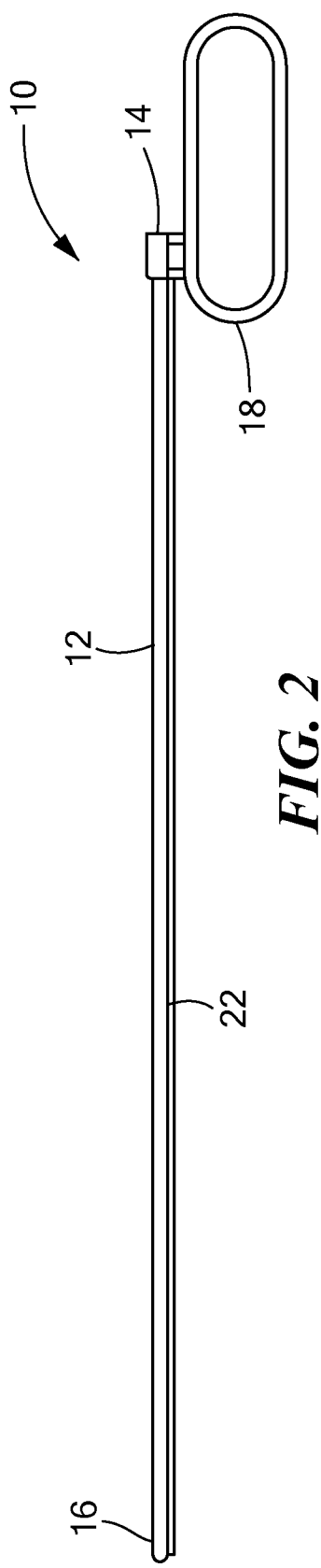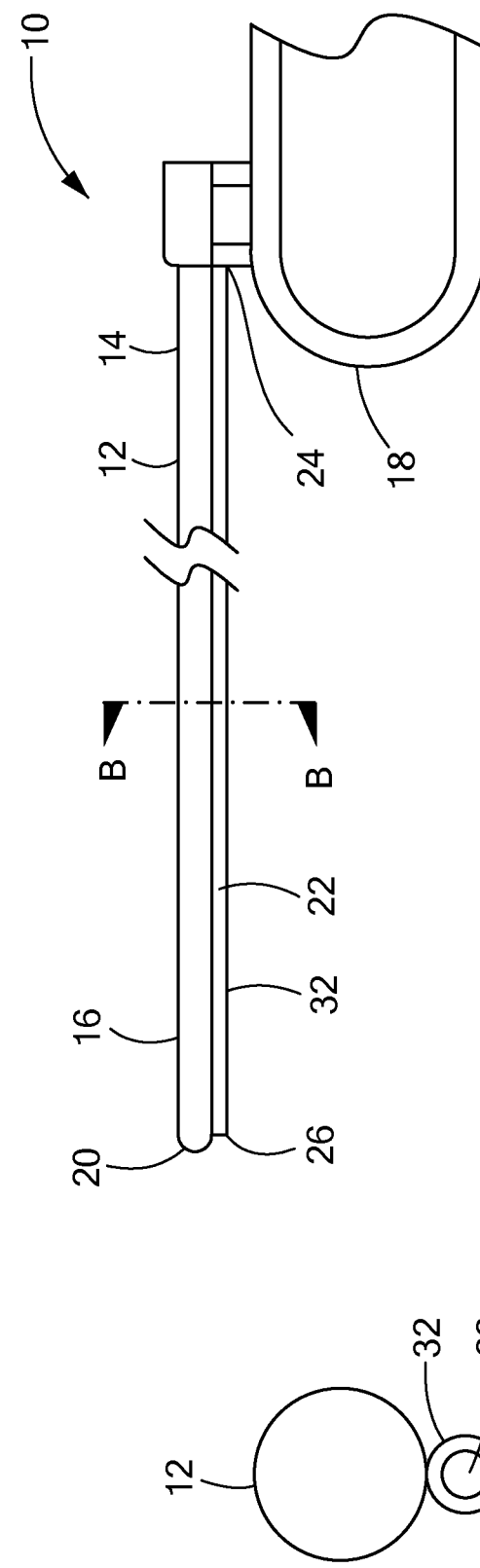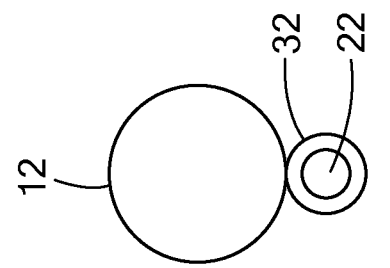

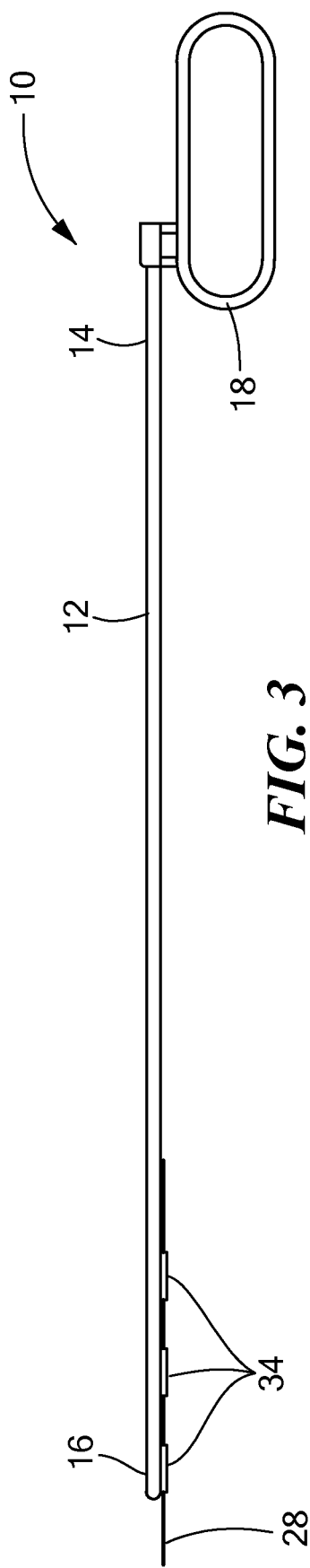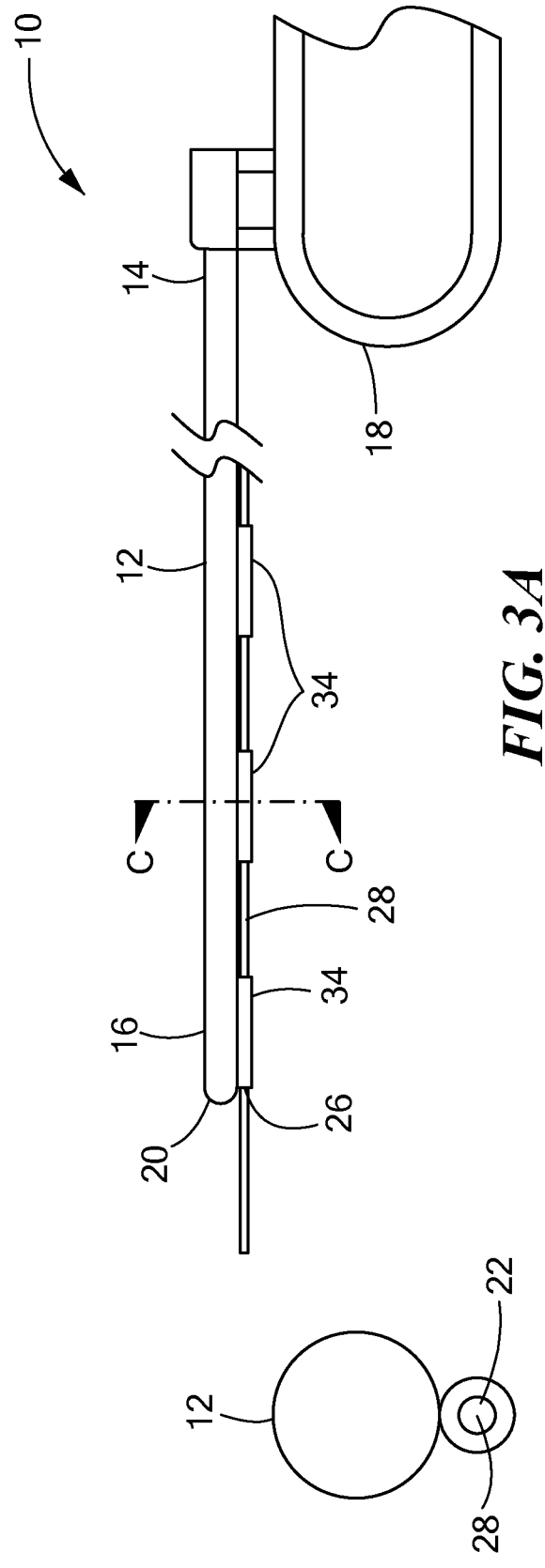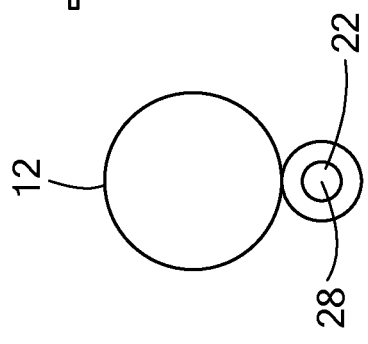

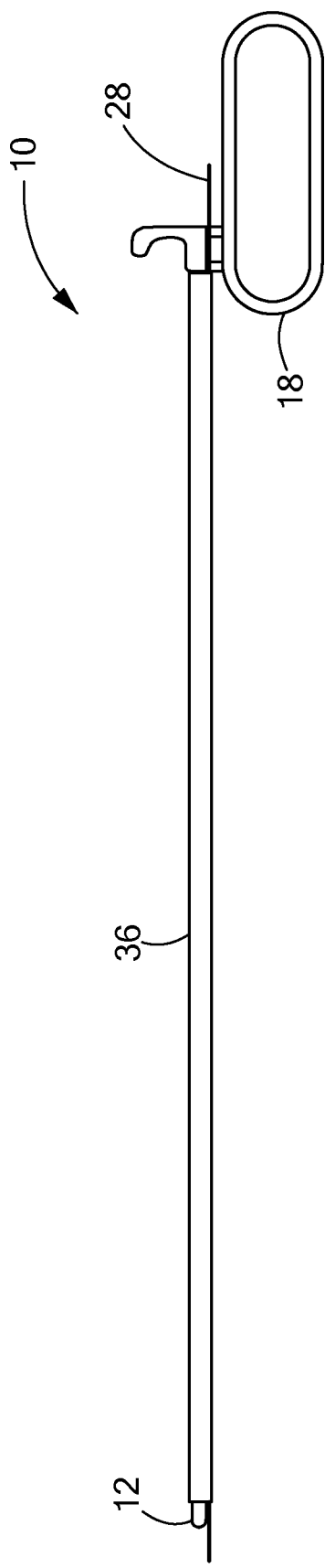
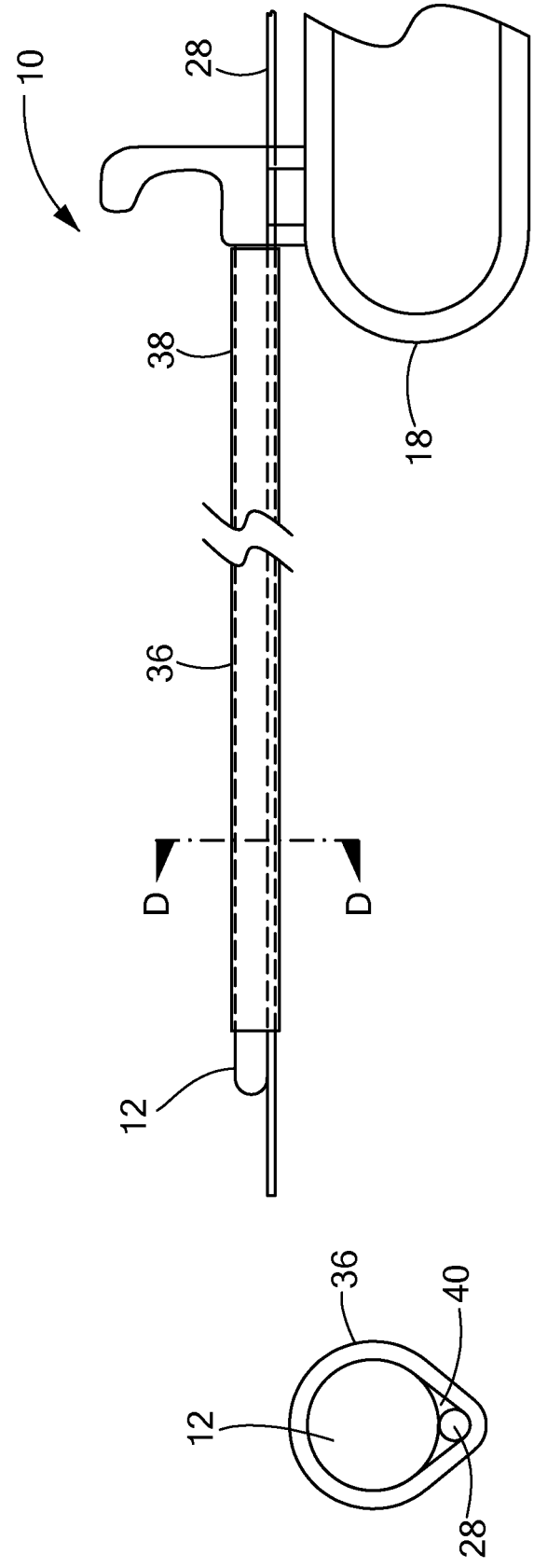
FIG. 4
FIG. 4A
FIG. 4B

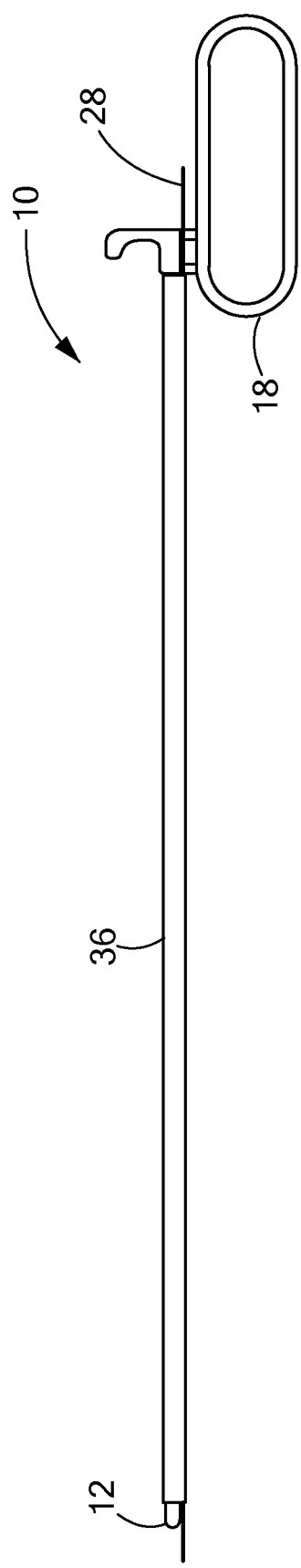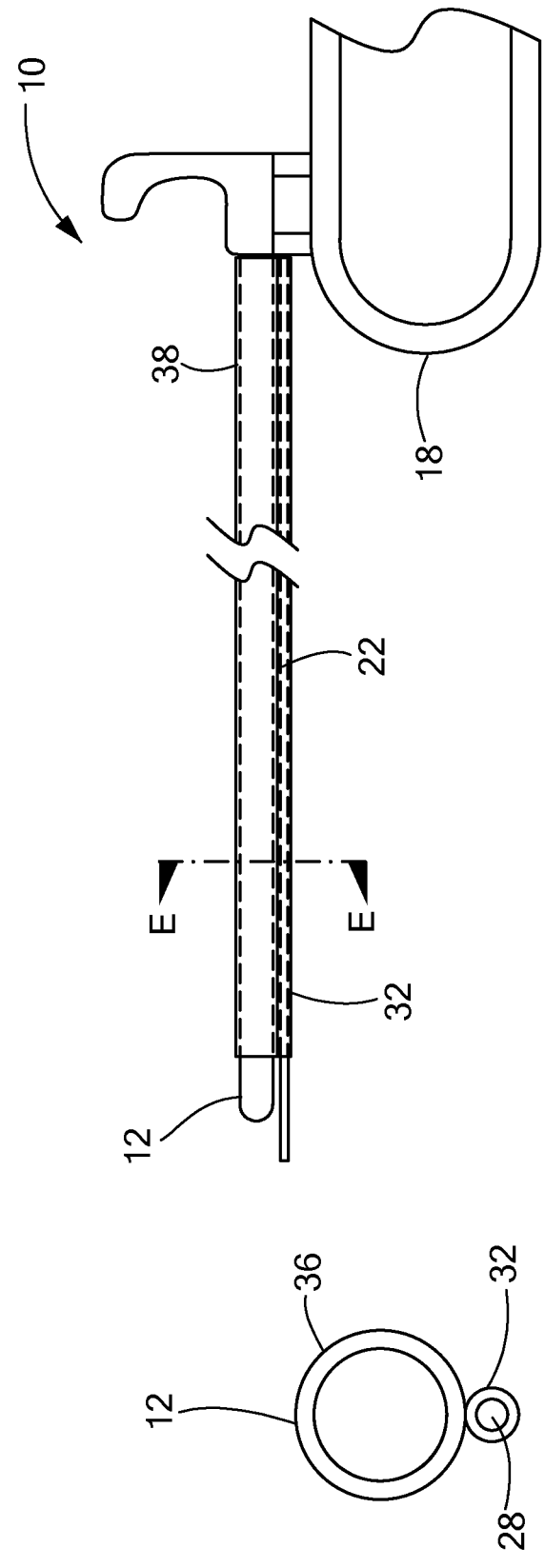

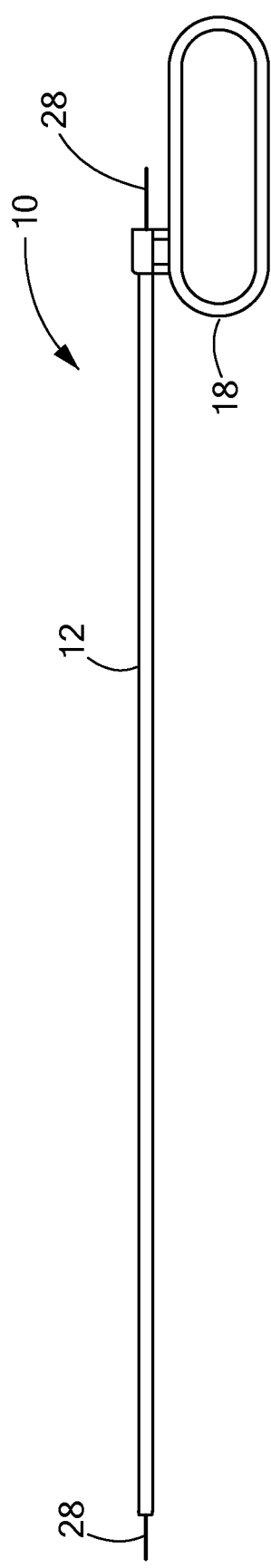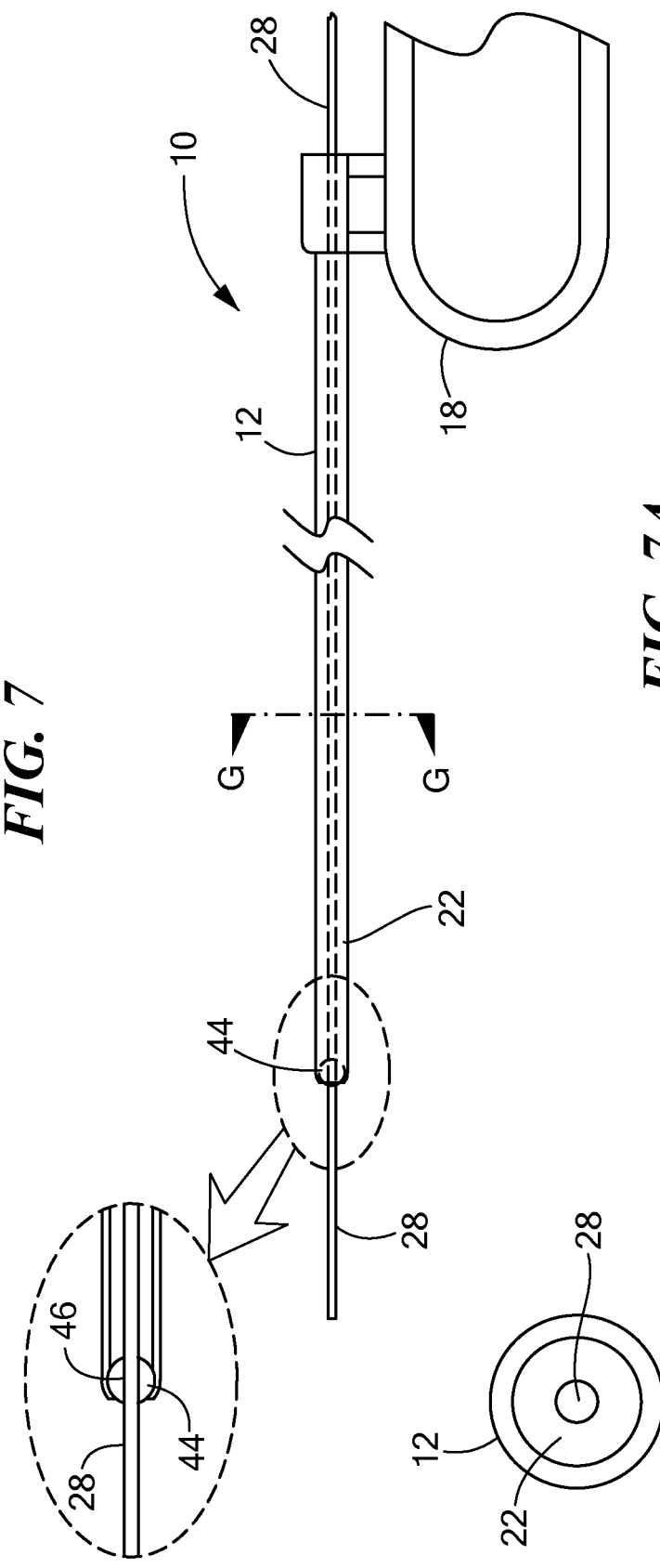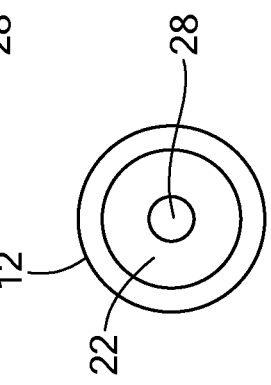
FIG. 7
FIG. 7A
FIG. 7B

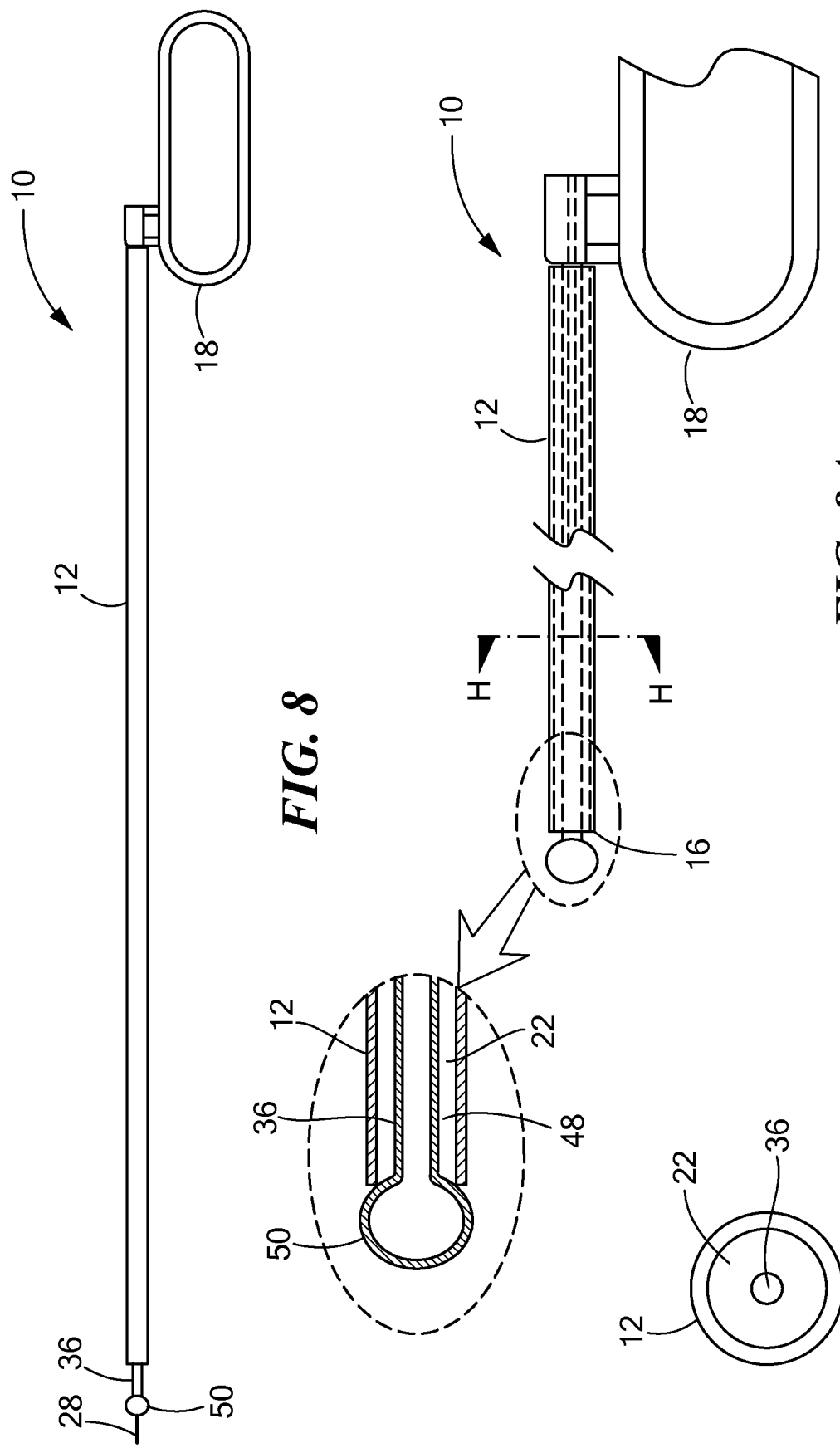

US 10,842,988 B2

OVER-THE-WIRE DELIVERY OF A SUBSTERNAL LEAD

CROSS-REFERENCE TO RELATED APPLICATION n/a

STATEMENT REGARDING FEDERALLY SPONSORED RESEARCH OR DEVELOPMENT n/a

FIELD OF THE INVENTION

The present application relates to methods and medical devices for substernal implantation of a medical lead.

BACKGROUND OF THE INVENTION

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter defibrillator (ICD) system has been shown to be beneficial at preventing SCD. An ICD system includes an ICD, which is a small battery powered electrical shock device, may include an electrical housing, or can electrode, that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, methods have been devised to achieve a similar effect to that of a transvenous ICD system connected directly to the heart without placing electrical lead wires within the heart or attaching electrical wires directly to the heart.

Subcutaneous implantable cardioverter-defibrillator (SubQ ICD) systems have been devised to deliver electrical impulses to the heart by the use of a defibrillation lead placed subcutaneously on the torso. However, the SubQ ICD is large and requires an output of around 80J of energy to be effective. The large size of the SubQ ICD compromises patient comfort and has been known to erode through the skin after implantation. In addition, the SubQ ICD system is incapable of delivering anti-tachycardia pacing (ATP), which is a standard therapy in transvenous ICDs to painlessly terminate lethal tachyarrhythmias. Owing to the large size and cost of the SubQ ICD device and its inability to deliver painless therapy, it is desirable to provide a medical system that does not require such a large output of energy for defibrillation and which can deliver ATP.

SUMMARY OF THE INVENTION

The present application advantageously provides methods and medical devices for implanting a substernal medical lead. In one embodiment, the method includes advancing a tunneling tool posteriorly proximate the caudal end of the sternum toward a first location. The tunneling tool is advanced superiorly underneath the sternum through the anterior mediastinum from the first location to a second location cranial to the first location. A guidewire is advanced from the first location to the second location. A medical lead is slid along at least a portion of the guidewire, the medical lead at least substantially spans the distance between the first location and the second location.

In another embodiment, the medical device includes a tunneling tool having a proximal portion, a distal portion, and a lumen therethrough, the distal portion of the tunneling tool being at least one of bent and bendable. A guidewire is slideably receivable within the lumen, the guidewire being slideable within the lumen from the proximal end of the tunneling tool to a distance beyond the distal end of the tunneling tool. A medical lead is slideable about the guidewire.

In yet another embodiment, the method includes advancing a tunneling tool posteriorly proximate the manubrium toward a first location. The tunneling tool is advanced inferiorly underneath the sternum from the first location to a second location proximate the caudal end of the sternum. A guidewire is advanced from the first location to the second location. A medical lead is slid along at least a portion of the guidewire, the medical lead at least substantially spans the distance between the first location and the second location.

In yet another embodiment, the method includes advancing a tunneling tool having a proximal end, a distal end, and a lumen therethrough, posteriorly proximate the caudal end of the sternum toward a first location. The tunneling tool includes a filament disposed within the lumen spanning from the proximal end to the distal end of the lumen. The tunneling tool is advanced superiorly underneath the sternum through the anterior mediastinum from the first location to a second location cranial to the first location. The filament is withdrawn from the lumen and from the patient. A guidewire is advanced through the lumen from the first location to the second location, the guidewire is advanced out through the distal end of the tunneling tool. The tunneling tool is withdrawn from the patient. A medical lead having at least one of a loop and a central lumen is slid along at least a portion of the guidewire, the medical lead at least substantially spans the distance between the first location and the second location.

BRIEF DESCRIPTION OF THE DRAWINGS

A more complete understanding of the present application, and the attendant advantages and features thereof, will be more readily understood by reference to the following detailed description when considered in conjunction with the accompanying drawings wherein:

FIG. 1 is a side view of a tunneling tool constructed in accordance with the principles of the present application;

FIG. 1A is a side cross-sectional view of the tunneling tool shown in FIG. 1;

FIG. 1B is a cross-sectional view of section A-A shown in FIG. 1A;

FIG. 2 is a side view of another tunneling tool constructed in accordance with the principles of the present application;

FIG. 2A is a side cross-sectional view of the tunneling tool shown in FIG. 2;

FIG. 2B is a cross-sectional view of section B-B shown in FIG. 2A;

FIG. 3 is a side view of another tunneling tool constructed in accordance with the principles of the present application;

FIG. 3A is a side cross-sectional view of the tunneling tool shown in FIG. 3;

FIG. 3B is a cross-sectional view of section C-C shown in FIG. 3A;

FIG. 4 is a side view of another tunneling tool constructed in accordance with the principles of the present application;

FIG. 4A is a side cross-sectional view of the tunneling tool shown in FIG. 4;

FIG. 4B is a cross-sectional view of section D-D shown in FIG. 4A;

FIG. 5 is a side view of another tunneling tool constructed in accordance with the principles of the present application;

FIG. 5A is a side cross-sectional view of the tunneling tool shown in FIG. 5;

FIG. 5B is a cross-sectional view of section E-E shown in FIG. 5A;

FIG. 7 is a side view of another tunneling tool constructed in accordance with the principles of the present application;

FIG. 7A is a side cross-sectional view of the tunneling tool shown in FIG. 7;

FIG. 7B is a cross-sectional view of section G-G shown in FIG. 7A

FIG. 8 is a side view of another tunneling tool constructed in accordance with the principles of the present application;

FIG. 8A is a side cross-sectional view of the tunneling tool shown in FIG. 8;

FIG. 8B is a cross-sectional view of section H-H shown in FIG. 8A';

DETAILED DESCRIPTION OF THE INVENTION

Figure 6:
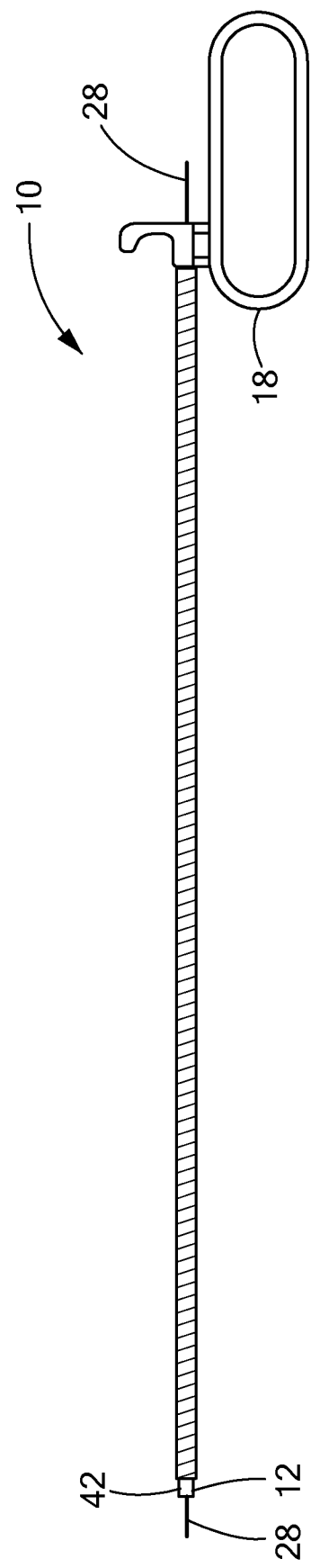
FIG. 6 is a side view of another tunneling tool constructed in accordance with the principles of the present application.
Figure 6A:
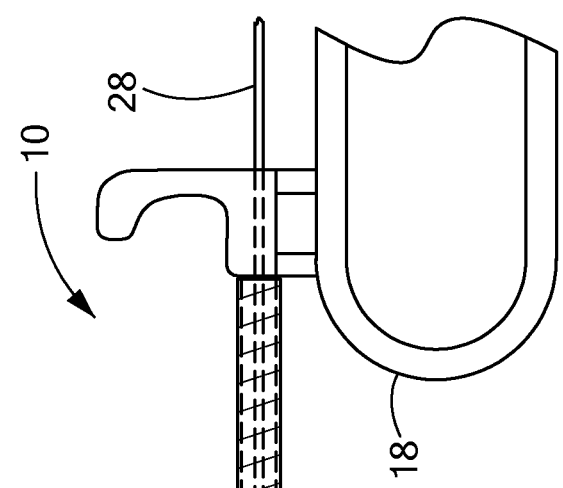
FIG. 6A is a side cross-sectional view of the tunneling tool shown in FIG. 6.

Referring now to the drawings in which like reference designators refer to like elements, there is shown in FIGS. 1-1B an exemplary medical device constructed in accordance with the principles of the present application and designated generally as "10." The medical device 10 may include a tunneling tool 12 sized to be received with the torso of a human or animal patient. In particular, the tunneling tool 12 may be a solid or hollow rod or shaft sized and configured to penetrate the fascia and the anterior mediastinum proximate the xiphoid process. The tunneling tool 12 may define a proximal end 14 and a distal end 16. The proximal end 14 may be coupled to a handle 18, which may be any shape or size sufficient for the surgeon to grip. In an exemplary configuration the handle 18 is coupled to the proximal end 14 and defines a closed loop.

The distal end 16 may be biased in a bent configuration or may be bendable depending on the composition of the tunneling tool 12. For example, the tunneling tool 12 may be substantially composed of a substantially rigid material such as stainless steel or plastic, or a flexible material such as Nitinol. In an exemplary configuration, the tunneling tool 12 is composed of substantially rigid metallic material and the distal end 16 is either biased or bent at an angle of approximately 30 degrees or bendable. For example, the bend may initiate from approximately 3-5 cm from the distal end 16. The distal end 16 may further define a tip 20, which may be blunted for atraumatic tunneling through the tissues of the torso, or may be beveled or otherwise define a sharp tip to facilitate dissection of tissue. In an exemplary configuration, the tip 20 defines at least a substantially conical shape for penetrating diaphragmatic attachments and connective tissue in the patient's torso. In other configurations the tunneling tool 12 terminates such that its distal end 16 defines a planar surface. The tip 20 may include a radiopaque marker (not shown) such that the position of the distal end 16 may be seen with fluoroscopy.

The tunneling tool 12 may further define a lumen 22 extending from the proximate end 14 to the distal end 16. For example, as shown in FIG. 1A, the lumen 22 extends completely through the length of the tunneling tool 12 such that there is a first opening 24 in the tunneling tool at the proximate end 14 and a second opening 26 at the distal end 16. In an exemplary configuration, the lumen 22 defines a diameter of approximately 0.5 mm and may be off-set from the center of the circumference of the tunneling tool 12 or may alternatively be co-axial with the center of the tunneling tool 12. For example, as shown in FIG. 1B, the lumen 22 is off-set from center of the tunneling tool 12 toward the upper portion of the interior of the tunneling tool 12. In other configurations the lumen 22 may be off-set any distance from the center of the tunneling tool 12 in any direction such that the tip portion of the conical tip is solid. In a particular configuration, the lumen 22 is off-set toward the upper portion of the tunneling tool 12 such that when the tunneling tool 12 is advanced through the anterior mediastinum tissue may be prevented from being wedged or otherwise forced into opening 26.

Continuing to refer to FIG. 1A guidewire 28 is included with the device 10, the guidewire 28 being sized to be slideably advanced through the lumen 22. The guidewire 28 may be composed of a superelastic material, such as Nitinol, or other flexible material and defines an outer diameter smaller than the inner diameter of the lumen 22. The guidewire 28 may further be resistant to axial compression forces such that it is pushable through the lumen 22 without bending. In an optional configuration, the guidewire 28 includes a loop (not shown) at its distal end. The loop is biased in the looped configuration, but is transitionable from a linear configuration when disposed within the lumen 22 to its looped configuration when advanced out through the distal end 16. The loop may define a larger diameter than that of the lumen 22 which may facilitate the removal of the tunneling tool 12 while leaving the guidewire 28 in place. Optionally, a filament 30 may be insertable within the lumen 22 during a procedure, or may be pre-disposed within the lumen 22 prior to insertion within the patient. The filament 30 may be composed of a polymer or other flexible material, and may be the same or similar diameter to that of the guidewire 28. In particular, the filament 30 may be sized to span the lumen 22 from the distal end 16 to the proximate end 14 of the tunneling tool 12 and is configured to at least substantially fluidly seal the lumen 22. For example, the filament 30 may be pre-disposed within the lumen 22 with a portion of the filament 30 extending beyond the proximal end 14 of the tunneling tool 12 out past the opening 24 or with the filament 30 being substantially co-terminus with the proximal end 14. In such a configuration, air may be prevented from entering the opening 24 of the lumen 22 from the outside of the patient because the filament 30 seals lumen 22. Additionally, the filament 30 may act to prevent blood from entering the distal end of the lumen 22 from the opening 26 as the filament 30 acts like a plug to seal the opening 26. Optionally, the filament 30 may be a resorbable material, for example, soft polyurethane, a suture, or mannitol, plugged within the opening 26 at the distal end of the lumen 22. In this configuration, the filament 30 may be dislodged from the opening 26 when the guidewire 28 is slid out through the opening 26 and purging the filament from the distal end 16 to be dissolved within the body.

Referring now to FIGS. 2-2B, in another configuration, the tunneling tool 12 may include a smaller-diametered tube 32 coupled to its exterior, the tube 32 defining the lumen 22 therethrough. The tube 32 may be composed of the same or different material to that of the tunneling tool 12 and may further include a bend similar to that of the tunneling tool 12. The tube 32 may be welded or otherwise affixed to the bottom portion of the tunneling tool 12 when aligned with the handle 18 or affixed at any position along the exterior of the tunneling tool 12. The tube 32 may further be co-terminus with the distal end 16 or alternatively, may terminate at a position proximal to the distal end 16 such that the tip 20 may contact tissue without interference from the distal end of the tube 32. The tube 32 may further be composed of a material that is resistant to kinking when bent or deflected such that a substantially unobstructed pathway is maintained within the lumen 22 as the guidewire 28 is advanced through the lumen 22.

Referring now to FIGS. 3-3B, in another configuration, the tunneling tool 12 is substantially the same configuration to that shown in FIGS. 2-2B except that instead of the tube 32 being coupled or otherwise attached to the tunneling tool 12, a plurality of loops 34 may be included on the exterior surface of the tunneling tool 12. The plurality of loops 34 may be any shape or size, and in particular, may be ringed shape and define an inner diameter less than the inner diameter of the tunneling tool 12 sized to receive the guidewire 28, which is predisposed inside the plurality of loops 34 prior to insertion of the tunneling tool 12 into the patient. The plurality of loops 34 may be disposed on the lower surface of the tunneling tool 12 in the direction of the handle 18 or along any portion of the exterior surface of the tunneling tool 12. In an exemplary configuration, three loops 34 may be spaced an equidistance apart from each other proximate the distal end 16 of the tunneling tool 12. It is further contemplated that any number of loops 34 may be included on the tunneling tool 12 disposed along any portion of the exterior surface from the proximate end 14 to the distal end 16 and spaced any distance apart.

Referring now to FIGS. 4-4B, in another configuration, the device 10 includes a sheath 36 surrounding the tunneling tool 12. The sheath 36 may be composed of a sterile flexible material and extends at least substantially the entire length of the tunneling tool 12. The sheath 36 may be movably or immovably engaged to the exterior of the tunneling tool 12. For example, the sheath 36 may be scored with a plurality of slits 38 along its length such that it may be readily peeled off or slit off the tunneling tool 12 when positioned at the desired location. Alternatively, the sheath 36 may be movable, either manually or through an actuator such that the distal end of the tunneling tool 12 may be distal to the distal end of the sheath 36 when advanced within the patient.

In the configuration shown in FIGS. 4-4B, the guidewire 28 may be received within a space 40 between the exterior surface of the tunneling tool 12 and the interior of the sheath 36. For example, the sheath 36 may be sized or stretched to accommodate the guidewire 28 and/or filament 30 such that there is a friction fit within the space 40. In an exemplary use, both the tunneling tool 12 and the guidewire 28 may be advanced simultaneous as the tunneling tool 12 is advanced through the patient's torso. Alternatively, the guidewire 28 may be advanced sequentially after the tunneling tool 12 is advanced toward its desired position. For example, when the tunneling 12 and the sheath 36 are advanced toward a desired position, the guidewire 28 may be slid through the space 40 toward the desired location. The tunneling tool 12 and/or the sheath 36 may then be removed from the patient leaving the guidewire 28 in place.

Referring now to FIGS. 5-5B, in another configuration of the devices 10 shown in FIGS. 4-4B and in FIGS. 2-2B, the device 10 may include the tube 32 of FIG. 2 with the sheath 36 of FIG. 5 surrounding the tube 32 and the tunneling tool 12. In particular, the sheath 36 may define the tube 32 in that both the sheath 36 and the tube 32 may be composed of the same or similar flexible material and may both include the slits 40 on each of their respective surfaces such that both the tube 32 and the sheath 36 may be peeled away. Optionally, the tube 32 may be removeably coupled to the sheath 36 by, for example, a biocompatible adhesive or a mechanical connection such that the tube may be separated from the sheath 36 when advanced toward the desired location within the patient's torso.

Figure 6B:
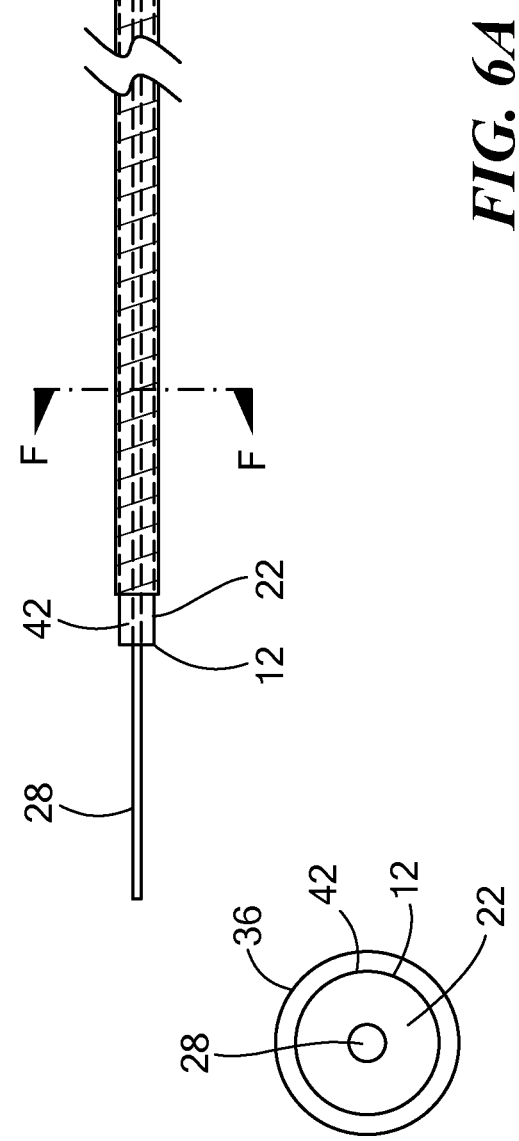
FIG. 6B is a cross-sectional view of section F-F shown in FIG. 6A.
Figure 9:
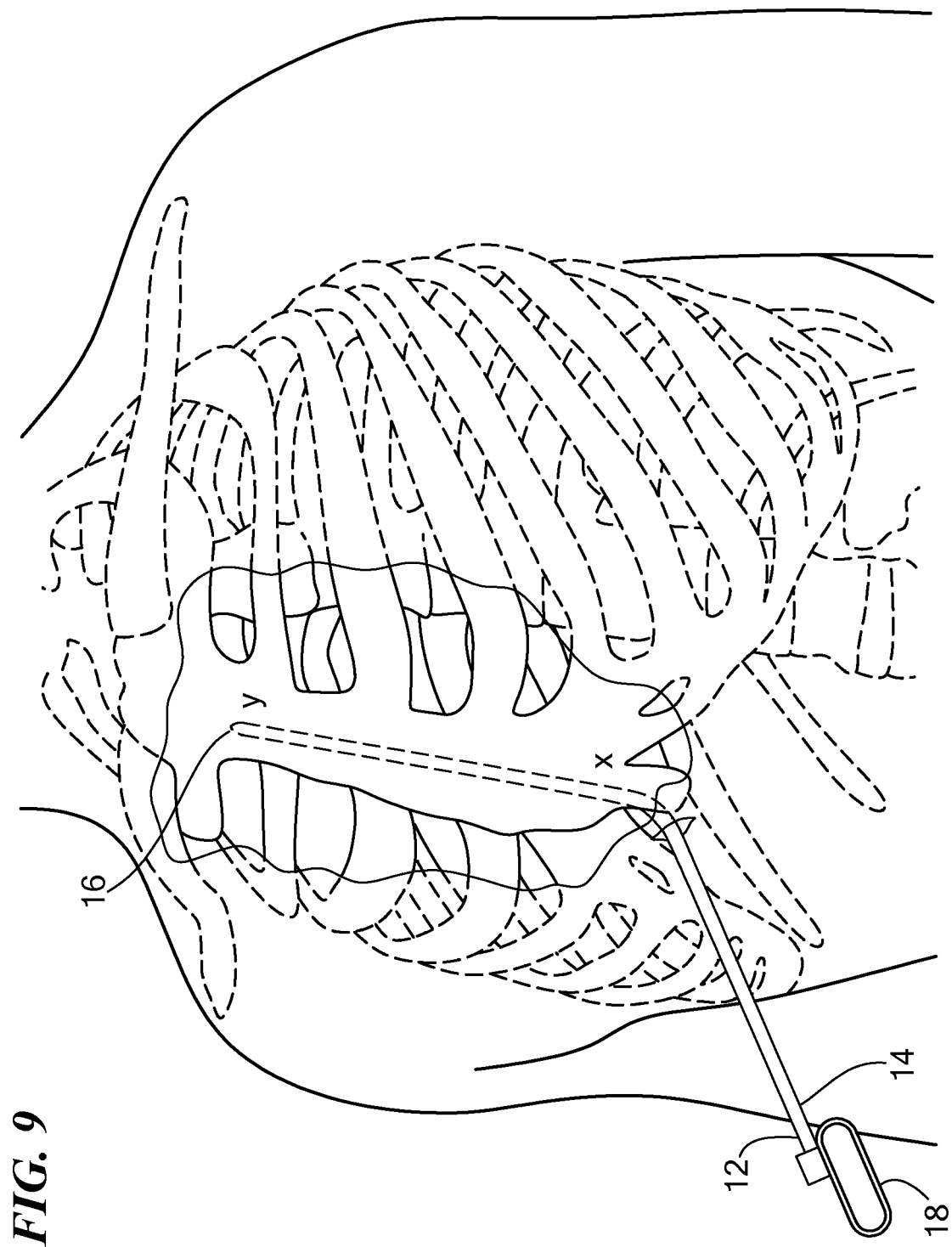
FIG. 9 is a perspective view of an exemplary patient's torso with the tunneling tool shown in FIG. 1A advanced substernally.
Figure 10:
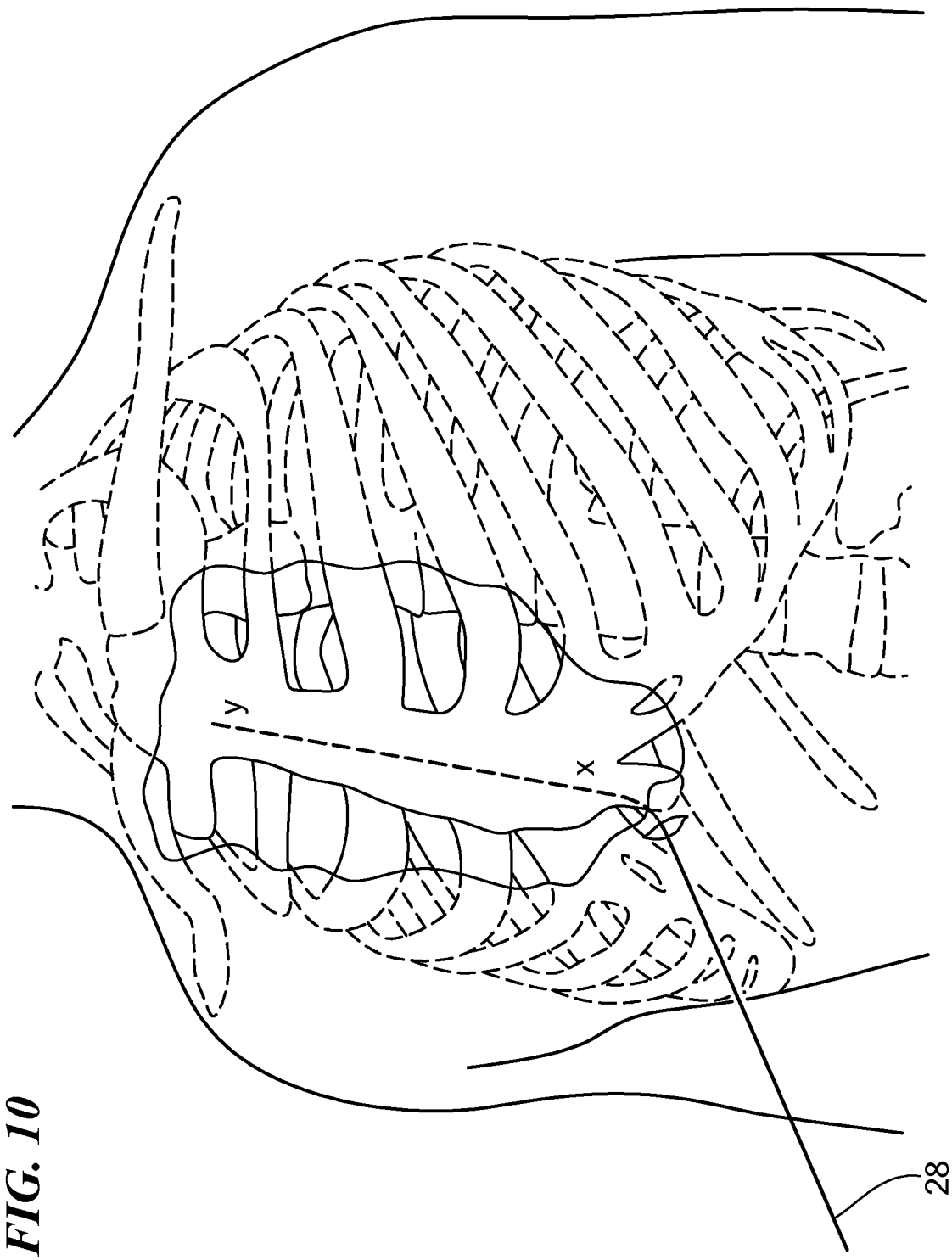
FIG. 10 is a perspective view of the exemplary patient's torso shown in FIG. 9 with a guidewire disposed substernally in the pathway created by the tunneling tool shown in FIG. 9.
Figure 11:
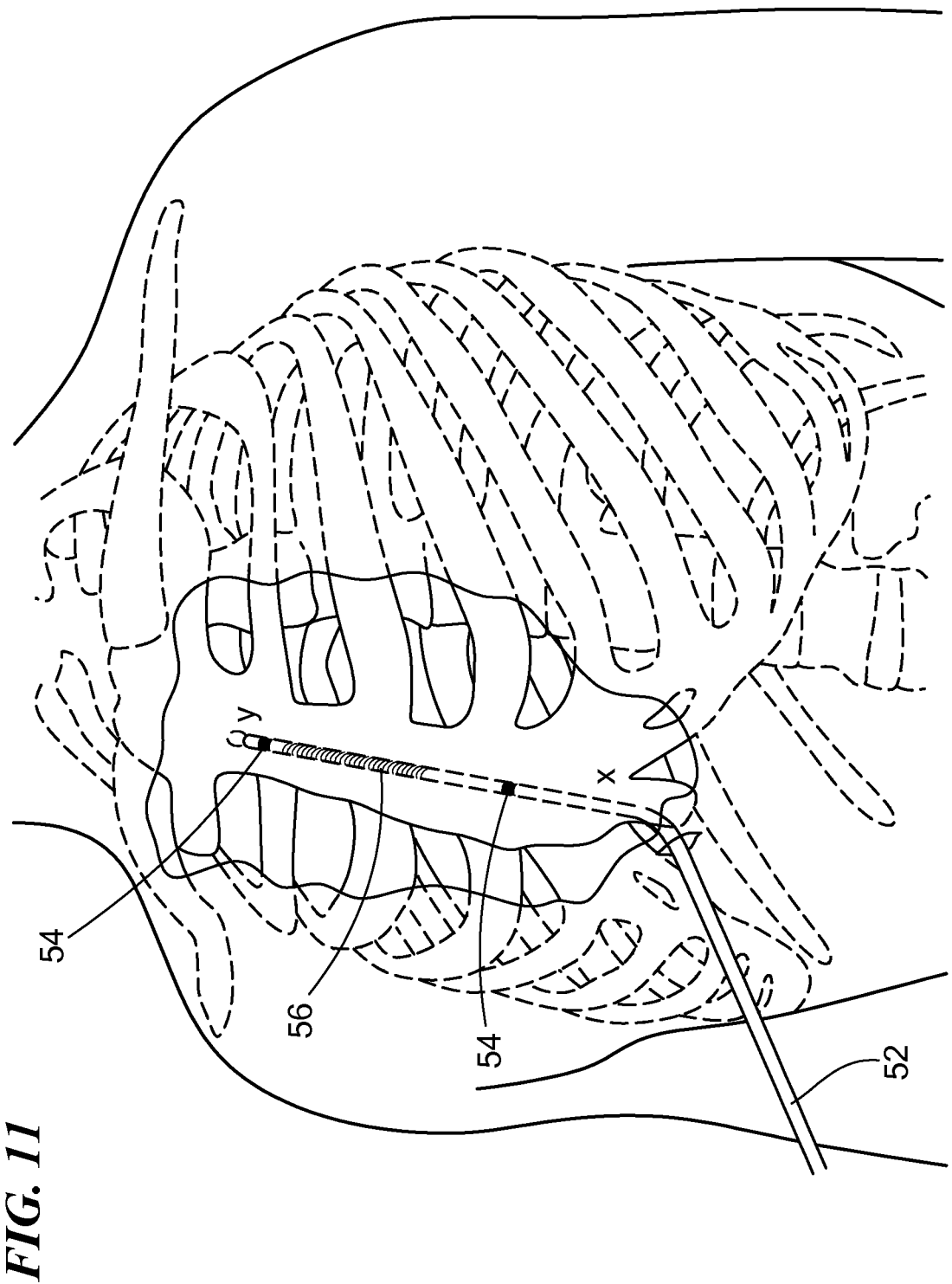
FIG. 11 is a perspective view of the exemplary patient's torso shown in FIG. 10 with a medical lead disposed in the pathway.
Figure 12:
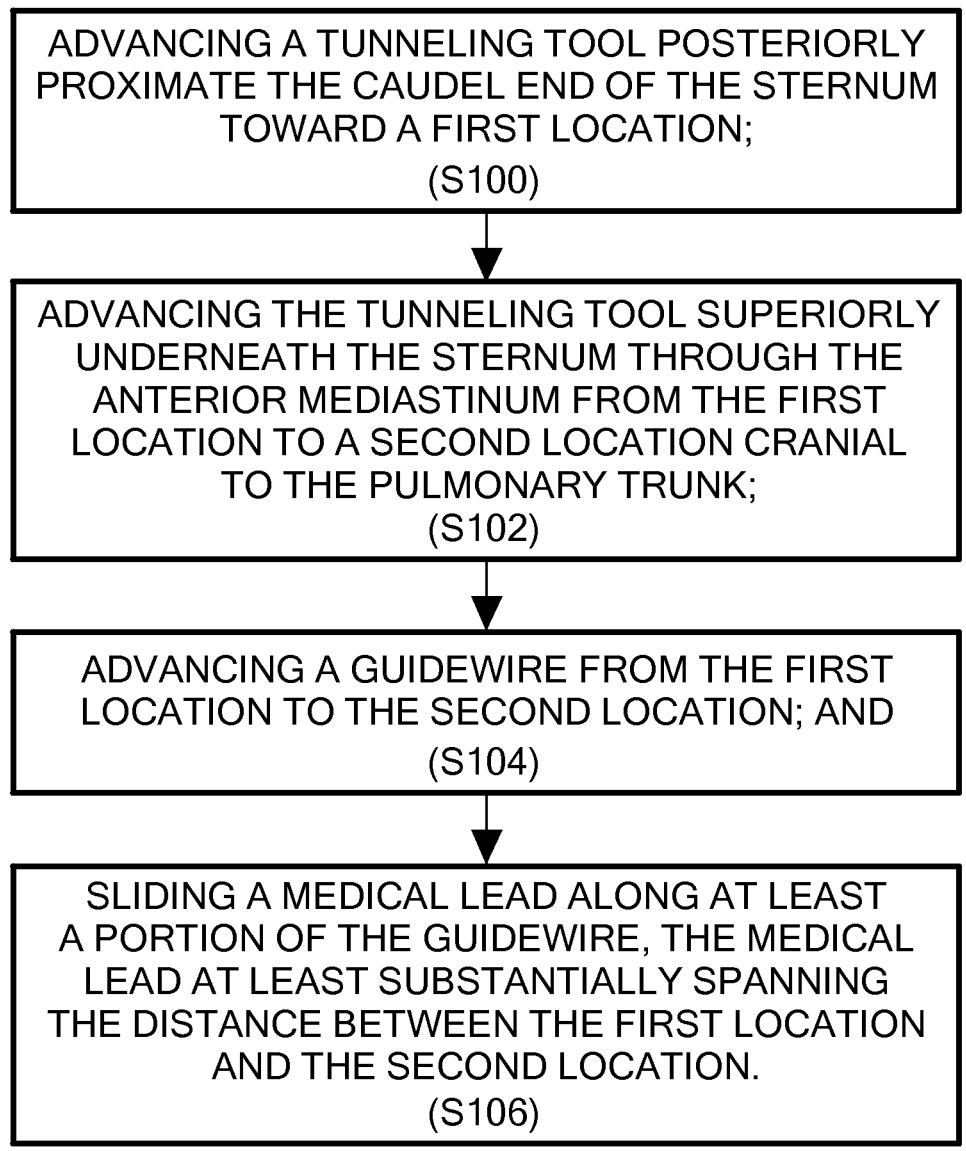
FIG. 12 is a flow chart of an exemplary method of implanting a substernal medical lead in accordance with the principles of the present application.

Referring now to FIGS. 6-6B, in another configuration, the tunneling tool 12 may be an over-the-wire deflectable catheter 42 received within the sheath 36. In particular, the catheter 42 may be braided or otherwise constructed such that a user may actuate an actuator (not shown) on the handle 18 to deflect the distal end of the catheter 42 toward any desired direction and to any desired angle including forming helical shapes. The catheter 42 may define the lumen 22 therethrough through which the guidewire 28 and/or filament 30 may be predisposed prior to insertion within the patient. The distal end of the catheter 42 may be blunted or sharp depending on its desired use. Moreover, the actuator may include an indicator to provide the user with indicia as to which direction the distal end of the catheter is deflected and to which angle.

Referring now to FIGS. 7-7B, in another configuration, the tunneling tool 12 may be hollow and define the lumen 22 therethrough. Disposed at the distal end of the tunneling tool 12 may be a tip member 44. The tip member 44 may be composed of a compressible biocompatible material such that it is friction fit within the lumen and self-expands to inhibit the flow of fluids into and out of the lumen 22. Optionally, the tip member 44 may further define a lubricious surface such that it is movable within the lumen 22 from the proximal end 14 to the distal end 16 and may further be pushed out the opening 26 into the patient where it may be degraded by the body. The tip member 44 may alternatively be immovable at the distal end 16 and provide an air-tight seal at the distal end 16. The tip member 44 may further define an expandable ring 46 through which the guidewire 28 may be either slid through or predisposed within. In an exemplary operation the guidewire 28 may be advanced out through the expandable ring 46 while the tip member 44 remains lodged within the lumen 22.

Referring now to FIGS. 8-8B, in another embodiment, the sheath 36 may define a smaller outer diameter to that of the outer diameter of the tunneling tool 12, such that the sheath is removeably insertable within the lumen 22 of the tunneling tool. The sheath 36 may define an inflation lumen 48 into which air or saline may be inserted to expand the sheath 36 to a desired diameter. For example, the sheath 36 may be inflated such that its outer diameter is substantially flush with the inner diameter of the tunneling tool 12 to prevent air and fluid from entering the lumen 22. Disposed at the distal end of the sheath 36 may be an expandable member 50 in fluid communication with the inflation lumen 48. The expandable member 50 may be a balloon composed of nylon, PeBax, or other similar material and may be expanded to a size larger than the outer diameter of the tunneling tool 12. For example, the expandable member 50 may be inflated when the distal end of the sheath 36 is advanced beyond the distal end 16 of the tunneling tool and then inflated. In such a configuration, the expandable member 50 operates to prevent the rigid tunneling tool 12 from damaging surrounding tissue as the tissue is first contacted by the expandable member 50 rather than the distal end 16 of the tunneling tool 12. When positioned proximate the target position, the sheath 36 and/or the expandable member 50 may be deflated and the guidewire 28 may be advanced through the inflation lumen 48.

Referring now to FIGS. 9-12, the user may use any one medical device 10 configurations discussed above, or a combination of features from any one of the medical devices 10, to implant or otherwise position a substernal medical lead within a human or animal patient. The method of implanting a medical lead, for example, a defibrillation lead 52 within the patient, includes advancing the tunneling tool 12 posteriorly proximate the caudal end of the sternum toward a first location (x) (S100). In particular, the surgeon may make an incision proximate the caudal end of the sternum, or in particular, the xiphoid process, and advance the medical device 10, or another medical device such as a dilator or other hypodermic device, into the patient. The surgeon may push the medical device 10 through the diaphragmatic attachments to reach the first location (x) which is underneath the sternum. In an exemplary configuration, the surgeon may use a bent or bendable tunneling tool 12, as described above, to tunnel from the incision point to the first location (x). Alternatively, the surgeon may make an incision on at least one of the left and the right side of the patient's torso and tunnel subcutaneously from the incision point to the first location (x).

The medical device 10 may be advanced superiorly underneath the sternum through the anterior mediastinum from the first location (x) to a second location (y) cranial to the first location (x). The extent to which the device 10 is advanced superiorly is dependent on the design of the medical lead 52 and the final placement of the lead 52 relative to the location of anatomical features of the heart. For example, in one embodiment, the medical lead 52 has an electrode, and a midpoint 56 of the electrode is 8 cm from the distal end of the lead 52. The final placement of the midpoint 56 of the electrode may be directly over the middle of the ventricle. Prior to placing the medical lead 52, the medical device 10 may be advanced to the second location (y) that is at least 8 cm cranial to the middle of the ventricle. Similarly, other designs of medical leads and final locations may require the advancement of the medical device 10 to different locations (y). Alternatively, a combination of one or more of the medical devices 10 discussed above may be used for steps S100 and S102.

One method to identify the second position (y) is to advance the distal tip of the medical device 10 until it is as cranial as the basal edge of the cardiac silhouette or a specific rib as seen on fluoroscopy. Alternatively, marking could be placed on the outside of the medical device 10 and the tool advanced a specified distance as determined by the markings. The filament 30, which may be included in the medical device 10 prior to insertion within the body, may then be withdrawn from the medical device 10 either by the surgeon pulling on the proximal end of the filament 30 or by the surgeon advancing a guidewire from the first location (x) to the second location (y) (S104) which may dislodge the filament 30 from the distal end of the medical device 100. A medical lead 52 may be slid along at least a portion of the guidewire (S106). In an exemplary configuration, the medical lead 52 at least substantially spans the distance between the first location (x) and the second location (y). The medical lead may be a defibrillation lead 52 having a plurality of electrodes 54, the medical lead 52 being electrically couplable to a can electrode (not shown) disposed within a subcutaneous pocket defined by the surgeon proximate the left armpit. The medical lead 52 may define a lumen therethrough or one or more rings on its exterior through which the guidewire 28 may be slid through. For example, when the surgeon positions the guidewire 28 in the desired position underneath the sternum, the medical lead 52 may be slid over the guidewire 28 to rest in the desired position underneath the sternum.

In an alternative configuration, the method of implanting a medical lead 52, for example, a defibrillation lead 52 within the patient, includes advancing a tunneling tool posteriorly proximate the manubrium toward a first location (x). In particular, the surgeon may make an incision proximate the manubrium proximate the midline of the patient, and advance the medical device 10, or another medical device such as a dilator or other hypodermic device, into the patient. Additionally, it is contemplated that first location (x) may be at any substernal position proximate the cranial end of the sternum or the manubrium. The tunneling tool 12 may be advanced inferiorly underneath the sternum from the first location (x) to a second location (y) proximate the caudal end of the sternum. The remainder of the method of implanting a medical lead 52 via the manubrium may include the same steps and medical device as those for implanting the medical lead proximate the caudal end of the sternum discussed above.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of implanting a substernal lead within a patient, the lead having at least two electrodes and defining a major longitudinal axis, the patient having a heart, sternum, a caudal end of the sternum, a cranial end of the sternum, and an anterior mediastinum, and a pulmonary trunk, the method comprising:

advancing a tunneling tool posteriorly proximate the caudal end of the sternum toward a first location within the anterior mediastinum;

advancing the tunneling tool superiorly underneath the sternum through the anterior mediastinum from the first location to a second location cranial to the first location and anterior to the heart;

advancing a guidewire from the first location to the second location;

sliding the lead along at least a portion of the guidewire; and implanting the lead underneath the sternum, the lead being advanced to a position:
   adjacent a posterior side of the sternum,
   spanning the distance between the first location and the second location when implanted, and;
   at which the at least two electrodes are disposed directly on the lead and along the major longitudinal axis.

2. The method of claim 1, further including creating an incision proximate the caudal end of the sternum through which the tunneling tool is advanced.

3. The method of claim 1, wherein the tunneling tool is at least one of a steerable catheter and a rigid tube.

4. The method of claim 1, further including advancing the tunneling tool subcutaneously from the left side of the patient's torso toward the caudal end of the sternum.

5. The method of claim 1, wherein the tunneling tool includes a lumen on its exterior sized to slideably receive the guidewire, and wherein advancing the guidewire from the first location to the second location includes advancing the guidewire through the lumen on the tunneling tool.

6. The method of claim 1, wherein the tunneling tool is at least one of a rigid tube and a catheter having a deflectable distal end, and wherein the tunneling tool defines a lumen therethrough and an opening at its distal end, and wherein advancing the guidewire from the first location to the second location includes advancing the guidewire through the lumen of the tunneling tool and out through the opening of the distal end of the tunneling tool.

7. The method of claim 6, wherein the tunneling tool defines an expandable ring at the distal end of the lumen, and wherein advancing the guidewire from the first location to the second location includes advancing the guidewire through the expandable ring.

8. The method of claim 1, wherein the tunneling tool includes a plurality of rings spaced a distance away from each other along the length of the exterior of the tunneling tool, and wherein advancing the guidewire from the first location to the second location includes advancing the guidewire through the plurality of rings.

9. The method of claim 1, wherein the tunneling tool includes a sheath disposed around its exterior, and wherein the guidewire is disposed in a space between the interior of the sheath and the exterior of the tunneling tool, and wherein advancing the guidewire from the first location to the second location includes advancing the guidewire through the space between the interior of the sheath and the exterior of the tunneling tool.

10. The method of claim 1, wherein the tunneling tool includes a sheath disposed around its exterior, and wherein the sheath includes a lumen on its exterior sized to slideably receive the guidewire, and wherein advancing the guidewire from the first location to the second location includes advancing the guidewire through the lumen on the sheath.

11. The method of claim 1, wherein the tunneling tool defines a lumen therethrough and includes a blunt tip at its distal end, and wherein advancing the guidewire from the first location to the second location includes advancing the guidewire through the lumen of the tunneling tool and out through the tip.

12. The method of claim 1, wherein the lead includes at least one electrode proximate a distal end of the lead and wherein sliding the lead along at least the portion of the guidewire comprises sliding the distal end of the lead along at least the portion of the guidewire to place the distal end of the lead at the second location.

13. The method of claim 1, wherein the first location and the second location spans at least a majority of a distance between the caudal end of the sternum and the cranial end of the sternum.

14. The method of claim 1, wherein the lead includes at least one electrode and wherein implanting the lead underneath the sternum comprises implanting the lead underneath the sternum such that the at least one electrode is located within the anterior mediastinum.

15. The method of claim 1, wherein the second location is proximate the cranial end of the sternum.

16. A method of implanting a substernal lead within a patient, the lead having at least three electrodes and defining a major longitudinal axis, the patient having a heart, sternum, a caudal end of the sternum, a cranial end of the sternum, and an anterior mediastinum, the method comprising:

advancing a tunneling tool posteriorly proximate the caudal end of the sternum toward a first location;

advancing the tunneling tool superiorly underneath the sternum through the anterior mediastinum from the first location to a second location cranial to the first location and anterior to the heart;

advancing a guidewire from the first location to the second location;

sliding the lead along at least a portion of the guidewire; and implanting the lead underneath the sternum, the lead having the at least three electrodes directly coupled thereon, the lead being implanted such that the at least three electrodes are located within the anterior mediastinum, the lead is adjacent a posterior surface of the sternum, and, during use, the at least three electrodes are disposed along and parallel to the major longitudinal axis.

17. The method of claim 16, wherein the second location is proximate the cranial end of the sternum.

* * * * *